(12) United States Patent
Linsen et al.

(10) Patent No.: US 7,029,164 B2
(45) Date of Patent: Apr. 18, 2006

(54) AUTOMATED SYSTEM AND PROCESS FOR THE PREPARATION OF A HIGH VISCOSITY FLUID FORMULATION

(75) Inventors: Michael William Linsen, North Wales, PA (US); Mark Richard Schure, Blue Bell, PA (US); Kristin Weidemaier, Raleigh, NC (US)

(73) Assignee: Rohm and Haas Company, Philadelphia, PA (US)

( * ) Notice: Subject to any disclaimer, the term of this patent is extended or adjusted under 35 U.S.C. 154(b) by 223 days.

(21) Appl. No.: 10/414,357

(22) Filed: Apr. 15, 2003

(65) Prior Publication Data

US 2003/0198125 A1 Oct. 23, 2003

Related U.S. Application Data

(60) Provisional application No. 60/373,285, filed on Apr. 17, 2002.

(51) Int. Cl.
*B01F 7/02* (2006.01)
*B01F 15/02* (2006.01)

(52) U.S. Cl. .............. 366/152.1; 366/160.2; 366/181.8; 366/182.1; 366/261; 366/285

(58) Field of Classification Search ............. 366/152.1, 366/138, 285, 279, 311, 261, 160.2, 160.5, 366/177.1, 181.8, 182.2, 182.3, 182.4
See application file for complete search history.

(56) References Cited

U.S. PATENT DOCUMENTS 2,513,562 A * 7/1950 Holuba .................... 366/152.1

| 3,565,286 | A |   | 2/1971  | Latham, Jr. |
| 3,876,340 | A |   | 4/1975  | Thomas |
| 4,872,353 | A | * | 10/1989 | Orr et al. .................... 366/140 |
| 4,968,420 | A | * | 11/1990 | Mills et al. ............... 366/152.4 |
| 5,273,583 | A | * | 12/1993 | Langlois et al. ............... 366/17 |
| 5,525,305 | A | * | 6/1996  | Minekus et al. ............ 366/149 |
| 5,647,391 | A | * | 7/1997  | Chan et al. .............. 366/152.4 |
| 5,823,669 | A | * | 10/1998 | Jones .......................... 366/132 |
| 5,851,291 | A | * | 12/1998 | Poterala et al. ............. 366/304 |
| 5,914,047 | A | * | 6/1999  | Griffiths ..................... 366/341 |
| 5,935,332 | A | * | 8/1999  | Caucal ..................... 366/152.1 |
| 5,993,054 | A | * | 11/1999 | Tan et al. ................ 366/152.1 |

FOREIGN PATENT DOCUMENTS

| DE | 32 37 785 A | 9/1983 |
| DE | 38 40 260 A | 5/1990 |
| EP | 1 186 534   | 3/2002 |

* cited by examiner

*Primary Examiner*—Tony G. Soohoo
(74) *Attorney, Agent, or Firm*—Richard R. Clikeman; JoAnne P. Will

(57) ABSTRACT

An automated fluid formulating system for use in small scale laboratory operations. The system utilizes a computer to provide precise control over the measurement of ingredients and the entire formulating process. The novel feature of this invention is that it can provide precise control over the formulating of high viscosity, high solid fluids, such as emulsions and gels. Further, a pre-programmed cleaning cycle can be input into the computer to automatically clean the mixing elements so that the mixing elements do not contaminate subsequent formulations with materials from the prior formulation.

6 Claims, 3 Drawing Sheets

AUTOMATED SYSTEM AND PROCESS FOR THE PREPARATION OF A HIGH VISCOSITY FLUID FORMULATION

CROSS REFERENCE TO RELATED PATENT APPLICATIONS

This is a non-provisional application of prior pending U.S. provisional application Ser. No. 60/373,285 filed Apr. 17, 2002.

The present invention relates to a system for the preparation of fluid formulations. Specifically, it relates to small scale equipment, such as might be utilized in a laboratory, for the preparation of small quantities of fluid formulations. The invention integrates a computer with the mechanical formulation equipment to provide an accurate and reproducible method for the preparation of these fluid formulations.

BACKGROUND OF THE INVENTION

Small or laboratory scale automated fluid formulating devices are known in combinatorial chemistry operations, the pharmaceutical industry, and in high throughput screening systems used in agricultural and other such similar research areas. The common thread through all of these areas of technology is that the fluids they deal with have very low solids and very low viscosities. These fluids, as typified by water, have viscosities that are independent of the shear rate and generally have viscosities of 1 centipoise. These are referred to as Newtonian fluids because their viscosities are shear independent.

When attempting to formulate high viscosity, high solids fluids, such as slurries and colloids, certain inherent design and processing elements preclude the use of equipment which is commonly used for processing Newtonian fluids. When the fluid is Newtonian, the dispensing and mixing system can consistently and accurately measure whatever amounts might be called for. Problems result from the fact that non-Newtonian fluids, such as slurries and gels, are very shear sensitive. When high viscosity, high solids fluids are subjected to the shear forces caused by forcing these types of fluids through tubing under pressure, the viscosities of such fluids will change. This alteration in viscosity is unpredictable and will impact the measurement of the fluids moving through the tubing. Shear variations can distort volumetric measurements of these fluids. Since devices that measure out quantities of fluid ingredients based on volume are very sensitive to changes in viscosity, the accuracy of each measured aliquot cannot be assured, whether it's for a single dose in a specific formulation or for repeated doses in multiple formulations. The final formulation sample might therefore not correspond exactly to the desired formulation.

It is also important for the proper functioning of volume sensing systems that they remain free of fouling or clogging of their internal components. The cleaning of mixing devices designed for use with low viscosity, low solids fluids may be accomplished with ease. Cleaning is simply achieved by flushing internal components with water or a suitable solvent. Another problem that must be addressed when processing high viscosity, high solids fluids in the system described above relates to the issue of cleaning. High viscosity, high solids fluids will form films on the internal surfaces of the components of fluid dispensing and mixing systems designed to process low viscosity fluids. These films are very difficult to remove by simple flushing. Disassembly of the clogged components is often the only way to remove these deposits. Even this process, however, is only of value for a relatively short time because deposition will occur over and over. If not kept clean, these material deposits on internal tubing or at the dispensing nozzles will severely restrict or completely stop the flow of fluids. Since these types of systems are volume sensitive, the film buildup will displace free flowing fluid. The inaccurate measurement of ingredients will then result, producing a formulation product which will not correspond to the desired formulation. The operator may not, if ever, become aware of this problem until numerous quantities have already been dispensed.

An attempt to resolve some of the aforementioned problems is manifested in a machine used for processing high viscosity colorants for paints. It is commonly referred to as a tinting machine and may be found in the paint department of a hardware store. This type of machine uses high pressure pumps to move high viscosity fluids. While changes in the viscosities of the various tints may be acceptable in a paint tinting operation, such viscosity variances, which then might cause inaccurate volumetric measurements, cannot be tolerated in a precision fluid formulation generating system.

Further, the number of ingredients which can be used as formulation precursors in devices such as tinting machines is limited by the maximum number of dispensing vessels that can be installed onto the device. If a change in one of the ingredients is required, the entire dedicated pump, fluid reservoir and tubing system would have to be removed and cleaned, which is very time and labor intensive. The ability to work with a large variety of fluid precursor ingredients is therefore severely restricted.

What is therefore needed is an automated fluid formulating system which can accommodate the processing of a great number and diversity of fluid precursor ingredients required to prepare high viscosity, high solids fluid formulations. The fluid formulating system must be able to accurately measure quantities of shear sensitive, high viscosity fluids, must be easy to clean when changing from one formulation to another without having to disassemble any part or section of the device.

SUMMARY OF THE INVENTION

In one aspect, the present invention features an automated system for the production of small scale quantities of high viscosity, high solids fluids. The system consists of the mechanical equipment needed to transport liquid precursor ingredients from their respective storage vessels to a mixing vessel. The system is controlled by a computer which regulates the delivery of precise amounts of precursor ingredients into the mixing vessel. Formulating data is input into the computer, which then sends output signals to the mechanical transport equipment to deliver the desired amounts of formulation ingredients to the mixing vessel. Sensors can be incorporated into the mixing vessel to monitor numerous physical properties of the fluid formulation as it is being mixed in real time so that, if needed, changes can be instantaneously made to the formulation recipe and/or processing cycle in order to optimize the desired physical characteristics of the desired fluid formulation.

The system of the present invention solves the problem of working with shear sensitive fluids by utilizing a combination of tubing, pumps and sensors designed to measure out precursor formulation ingredients based on the mass of the fluid being dispensed rather than its volume. Further, the sensor can measure other physical characteristics of the fluid formulation and make adjustments to the recipe or process as required.

The disruptive and time consuming process of cleaning the mixing equipment is solved by the present invention by pre-programming into the recipe process a cycle whereby the mixing components are first removed from the mixing vessel after each unique formulation recipe is produced and then conveyed to a cleaning vessel. Once the pre-programmed cleaning cycle has been completed, the computer will direct the mixing components back to the mixing vessel to help process the next formulation. During this automated cycle, no operator involvement is required. Further, by having dedicated tubing lines for each formulation precursor and having the fluid components sealed within their respective tubing lines, neither the tubing or the pump requires downtime for cleaning.

A second aspect of the present invention is a method for the preparation of small scale quantities of high viscosity, high solids fluids. Because the method is highly automated, it eliminates the need for unnecessary operator supervision, significantly improves the consistency of multiple batches of the same formulation and, by simplifying and expediting the cleaning process, markedly reduces the amount of time required to change from one formulation to the next.

DETAILED DESCRIPTION OF THE DRAWINGS

DESCRIPTION OF THE INVENTION

Figure 1:
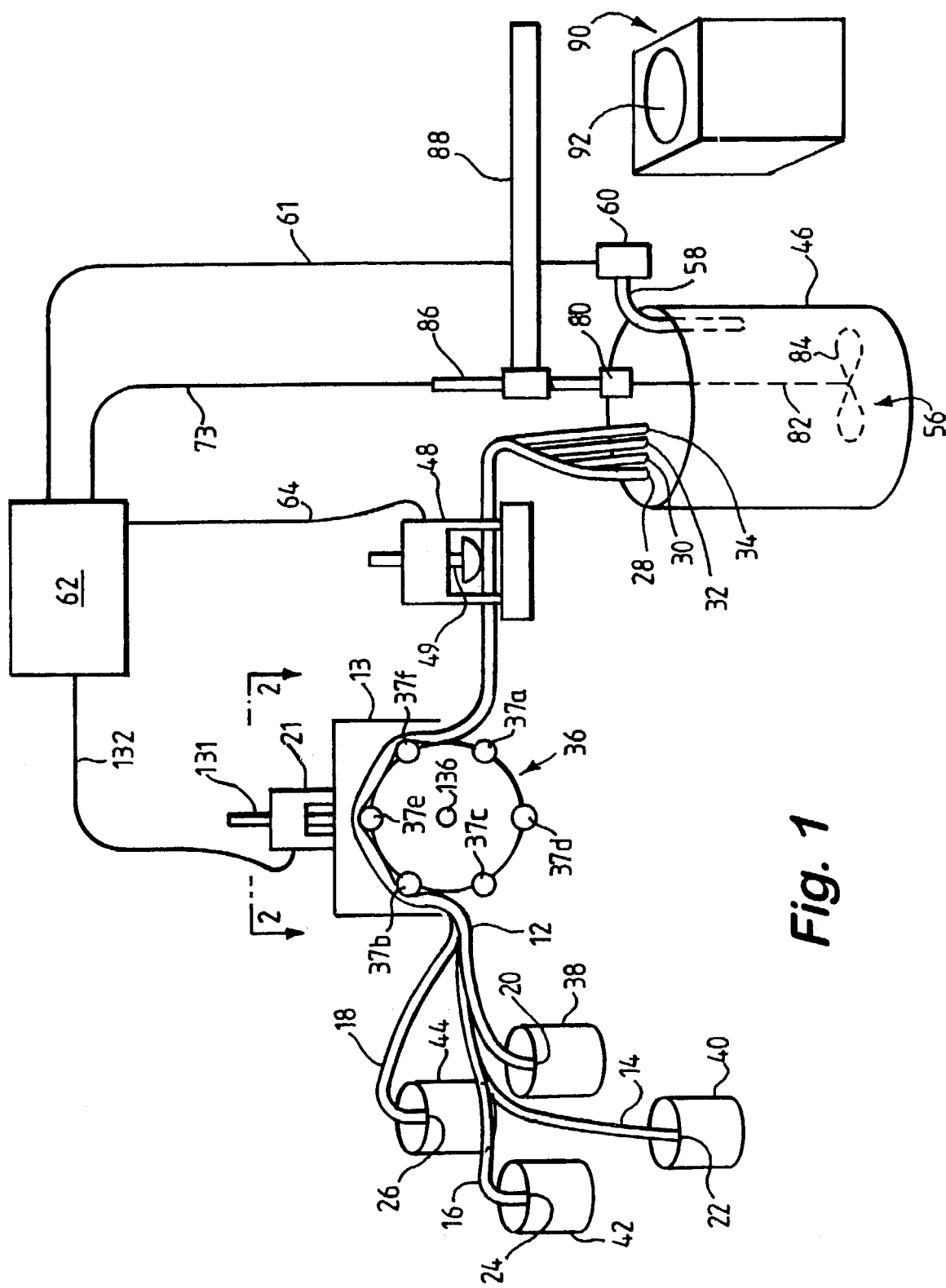
FIG. 1 is a general schematic of the entire fluid formulating system of the present invention.

FIG. 1 shows a system for making fluid formulations according to the present invention. The formulations that may be prepared by this system are high viscosity, high solids fluids. Examples of such fluids are emulsions, gels and colloids, which may have viscosities up to and including 10,000 poise.

The system is preferably used in a laboratory scale operation where, perhaps for evaluation and comparison purposes, many different fluid formulations must be prepared, each one differing from another by only minor changes in various physical properties, such as viscosity, mass, volume and pH. Alternatively, multiple samples of the same formulation could be prepared in this way with very exacting precision.

Each formulation would take considerable time to prepare when done by conventional means. Each separate precursor ingredient would have to be carefully measured, the mixing would have to be carefully monitored, perhaps requiring sample removal at various times in the commingling and mixing phases to insure that the desired final fluid properties are achieved.

The present invention combines the independent feeding of the various formulation precursor ingredients with an automated computer control system. An added feature of the automated computer control system is the real-time monitoring of the physical properties of the fluid formulation while mixing is occurring. Computer regulation, and if needed, feedback monitoring, of each precursor ingredient insures that the final fluid formulation is as close as practicable to the desired formulation. Precise repeatability is also an added benefit when multiple samples of the same formulation must be prepared.

Referring again to FIG. 1, the paint system consists of a plurality of flexible conduits 12, 14, 16 and 18, each having an inlet end 20, 22, 24 and 26, respectively, and an outlet end 28, 30, 32 and 34, respectively. While only four flexible conduit lines and their related equipment are shown, this is done solely for exemplifying the invention. It should be understood that more or less may be utilized in practice as required. These flexible conduits are operatively disposed within at least one of a plurality of pump means 36. Pump means are well known in the art. Various types of pumps may be employed in the practice of the present invention. Some suitable examples are progressive cavity pumps, such as those available from Moyno or Seepex, Peristaltic pumps, commercially available from MasterFlex and Watson-Marlow, syringe pumps, which are available from Sage and Harvard, diaphragm pumps, which may be acquired from KNF, gear pumps, available from Micropump and piston pumps, which are commercially available from Fluid Metering Inc. For the sake of merely exemplifying and not to limit the scope of the present invention only a single peristaltic pump is shown. For a more detailed description of representative peristaltic pumps, reference may be made to U.S. Pat. Nos. 4,025,241 and 4,365,943.

Each inlet end of each flexible conduit is disposed within one of a plurality of storage vessels 38, 40, 42, and 44. Each of these storage vessels contains a different liquid precursor ingredient, or combination of ingredients, which when mixed together will make up the desired fluid formulation.

The outlet ends 28, 30, 32 and 34 of the plurality of flexible conduits are positioned so as to deliver into a mixing vessel 46, each of the precursor ingredients respectively contained therewithin. The pump 36 is positioned between the storage vessels 38, 40, 42 and 44, and the mixing vessel 46 in order to facilitate the transfer of a precise amount of each of the precursor ingredients from its respective storage vessel into the mixing vessel 46.

Figure 2:
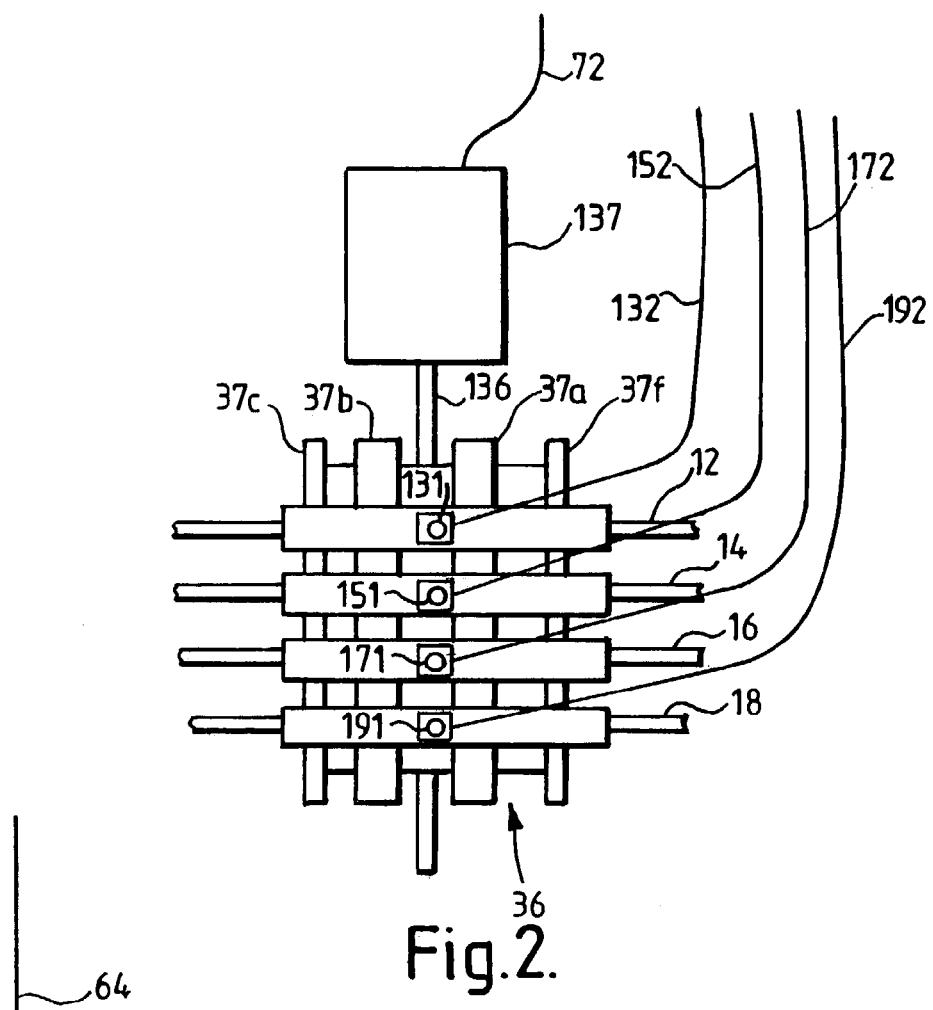
FIG. 2 is a top plan view of the pump means showing multiple flexible conduits and their corresponding flow restrictors taken along line 2—2 of FIG. 1.

The single peristaltic pump 36, as shown in FIGS. 1 and 2, consists of evenly spaced rollers 37a, 37b, 37c, 37d, 37e and 37f configured in a cylindrical shape equidistantly spaced around a central drive axle 136. Motor 137 drives axle 136 in a circular motion so that rollers 37a through 37f rotate around the axis of axle 136. Flexible conduits 12, 14, 16 and 18 are positioned over the rollers of the pump 36.

Each flexible conduit 12, 14, 16 and 18 is securely affixed to its own bracket assembly 13, 15, 17 and 19, respectively. Each bracket is disposed within a housing 21 and is capable of moving in a generally vertical direction under the independent control of a solenoid, a hydraulic system, pressurized gas or similar such means (hereinafter, "activation means"), 131, 151, 171 and 191, respectively. Activation means 131, 151, 171, and 191 are independently controlled by a computer 62 through lines 132, 152, 172 and 192, respectively. When each activation means 131, 151, 171, or 191 is activated, its respective bracket is urged in the direction of the pump 36. At the points of contact with the rollers 37a, 37b, 37c, 37d, 37e and 37f, the flexible conduits 12, 14, 16 and 18 are compressed, thereby restricting the flow of fluid while at the same time creating pockets of fluid between adjacent points of contact with each roller. When pump 36 is engaged, the rollers roll along the flexible conduits and move these pockets of fluid sequentially in a generally linear direction toward the mixing vessel 46. The pump 36 may also be run in reverse in order to return any one or all of the precursor fluids to their respective storage vessel if the formulation process has been completed or if one or more of the fluid precursors is to be exchanged for another fluid precursor.

Within the mixing vessel 46 is located means 56 for mixing the precursor ingredients to create the desired fluid formulation. The mixing means 56 which may be utilized in the practice of the present invention is one that is suitable for operation with small scale, laboratory equipment. Examples of such mixing means include overhead mixers, such as those available from Cole-Palmer Servodyne and IKA Laboratories, magnetic stirrers, such as might be acquired from Corning, rotor-stator homogenizers, available from Power-Gen, sonic homogenizers, commercially available from Thomas Scientific, and vortex mixers, available from Cole-Palmer. Solely for exemplary purposes and not to limit the scope of the invention, an overhead mixer is represented in FIG. 1. As shown, mixer 56 consists of a motor 80 connected through shaft 82 to one or more stirring blades, generally shown as 84. Mixer 56 is affixed to support bracket 88. Linear actuator and control means 86 regulates the vertical and lateral motion of the mixer 56. Linear actuator and control means 86 may consist of a stepper motor, a solenoid or a hydraulic valve. Linear actuator and control means 86 is capable of completely retracting mixer 56 from any contact with the mixing vessel 46.

Computer 62 is programmed to control the various process steps of the fluid formulating system of the present invention. The recipe, as it is commonly referred to, of the desired or hypothetical fluid formulation(s) is input into the database of computer 62 by various means such as manually by an operator, or from other database systems to which computer 62 is connected, such as a LIMS system (Laboratory Information Management System) or an expert system which is commonly used in coatings operations.

Another benefit of using a computer to control the fluid formulation system is that it may be programmed to monitor the entire formulating process and make adjustments to the rate of addition of the various precursor ingredients or to adjust the amount(s) of one or more of these ingredients. During mixing, it may be beneficial to monitor various physical properties of the fluid formulation as it is evolving. This is referred to as a feedback loop. Too much of one ingredient or not enough of another may totally alter the outcome of the desired formulation. Therefore, optionally, a multifunctional sensor means 58 may be installed within the mixing vessel 46 to quantitatively measure one or more of a plurality of physical properties of the fluid formulation. These physical properties are typically the overall mass, volume, viscosity and pH of the fluid formulation. The multifunctional sensor 58 is capable of converting each of the various measured physical properties into a corresponding measured physical property value. Since the sensor 58 may be programmed to operate continuously during the entire mixing cycle, it has the capability of providing a real-time analysis of the fluid as it is being formulated.

Attached to the sensor 58 is an electronic sending means 60 which transmits the measured physical property values to computer 62 via wire 61. As the computer 62 receives continuous feedback information from the sensor 58, it can generate a real-time analysis of a dynamic process. By dynamic it is meant that the various physical properties of the end product change over time as the various precursor ingredients are being added to the mixing vessel 46. The computer 62 receives measured physical property values transmitted by the sending means 60 and compares each measured physical property value to its corresponding desired physical property value. The desired physical property values have already been input into the computer database, as described hereinabove. If monitoring of the progress of the fluid formulation is desired by the operator, then the feedback loop between sensor 58 and computer 62 may be activated.

One of the most critical physical property values which can be measured by sensor 58 is the dynamic viscosity of the fluid formulation. Dynamic viscosity is a function of the torque resistance exhibited by the fluid as it is being formulated and will range from 1 centipoise to 10,000 poise. Poise is defined as a gram per centimeter second. Dynamic viscosity may also be measured in Pascal seconds, each unit defined as being a Newton second per square meter. For comparative relevance, 1000 Pascal seconds equals 10,000 poise.

Figure 3:
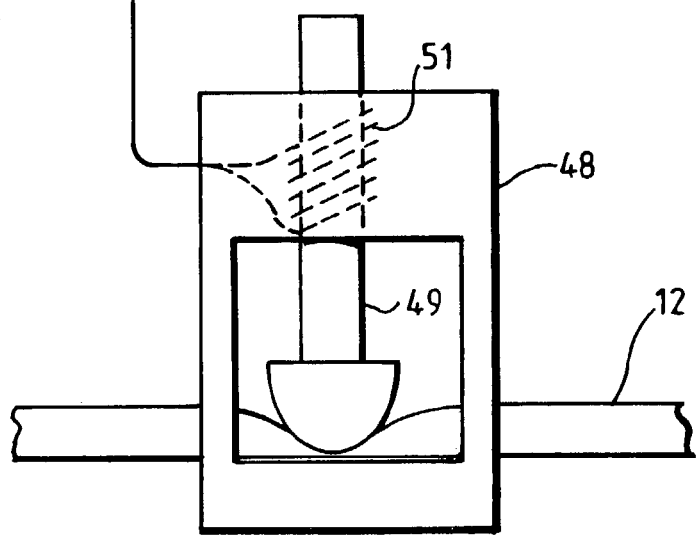
FIG. 3 is a close up cross-sectional view of one of the flow restrictors actuated to restrict the flow of fluid through its corresponding flexible conduit.

Whether or not the computer is operating solely on recipe information previously input into its database or is programmed to receive and process information continuously being fed back from the sensor 58 during formulating, the flow of the various precursor fluids through their respective flexible conduits must be carefully controlled. Referring to FIG. 2, separate flow restrictors 48, 50, 52, and 54 are operatively located on each of the plurality of flexible conduits to regulate the amount of each of the precursor ingredients being delivered to the mixing vessel 46. Although various designs of flow restrictors may be employed with the present invention, a preferred design, as shown in FIG. 3, comprises a valve plunger 49 which is operated by, for example, a hydraulic system, pressurized gas or solenoid means (hereinafter, "valve") 51. Each flow restrictor 48, 50, 52 and 54 is connected to computer 62 by electrically conductive wires 64, 66, 68 and 70, respectively. For example, in response to a signal from computer 62, sent via wire 64 to flow restrictor 48, the valve 51 is activated thus enabling the valve plunger 49 to forcibly contact and compress flexible conduit 12.

Depending on the directions provided by the computer 62, the valve plunger 49 may either only partially or completely obstruct the flow of fluid through flexible conduit 12. If flow in flexible conduit 12 is to be completely closed off, the computer will send a signal to activate flow restrictor 48, thus completely closing off the flow of fluid therethrough. Simultaneously, the computer 62 will send a signal through wire 132 to direct activation means 131 to retract bracket assembly 13 away from pump 36, thereby disengaging conduit 12 from contact with the pump rollers 37a through 37f. At this point, the movement of the specific fluid precursor contained within conduit 12 to the mixing vessel 46 will cease.

Alternatively, the computer 62, either in response to pre-programmed directions or to signals received from the sensor in the mixing vessel, may direct any one of the plurality of flow restrictors 48, 50, 52 or 54 to only partially restrict the flow of fluid through its respective flexible conduit, thus allowing only a reduced amount of the respective precursor ingredient to flow to the mixing vessel. As determined by the programming data fed into the computer, the addition of the ingredients into the mixing vessel may be performed either sequentially or serially.

By activating the feedback loop, the measured physical property values sent back to computer 62 are compared with their corresponding desired physical property values. Based on the difference, if any, between the measured and desired values, the computer 62 may be programmed to determine whether and, if so, how much more of any specific individual precursor ingredient might be needed to produce the desired fluid formulation having the proper balance of physical properties. For example, as the formulation is being mixed, the sensor 58 may detect that the dynamic viscosity is lower than was predicted for that point in the processing cycle. In such instance, more of the precursor ingredient which contains, for example, a thickener might be added to achieve the desired viscosity level.

As directed by the pre-programmed formulation protocol, the computer 62 will shut down the entire system once certain predetermined parameters are met, such as total mass, desired viscosity and/or target pH. Alternatively, if the sensor 58 is activated to feed real-time process information back to the computer 62, then once each of the physical properties which are being monitored equals its corresponding desired pre-programmed physical property value, then the delivery system is shut down. However, it may still be necessary, either according to a pre-programmed protocol or as determined by feedback information, to have the mixer remain on for an additional period of time, in order to satisfy the specific processing requirements for each formulation.

An additional essential feature of the inventive fluid formulation system is the ability to automate the process of cleaning the components of the mixer 56. As shown in FIG. 1, adjacent to the mixing vessel is a cleaning chamber 90. Cleaning chamber 90 contains an internal vessel 92 which holds a cleaning fluid. Any suitable cleaning chamber is within the contemplation of the present invention, such as ultrasonic chambers, agitating devices, internal spray washers or abrasion scrubbers. The cleaning fluid may be anything suitable for cleaning the residue of the fluid which has been formulated from the various surfaces of mixer 56. Such cleaning fluids may consist of water, hydrocarbon solvents, aqueous surfactants, supercritical fluids or any combination thereof.

Figure 4:
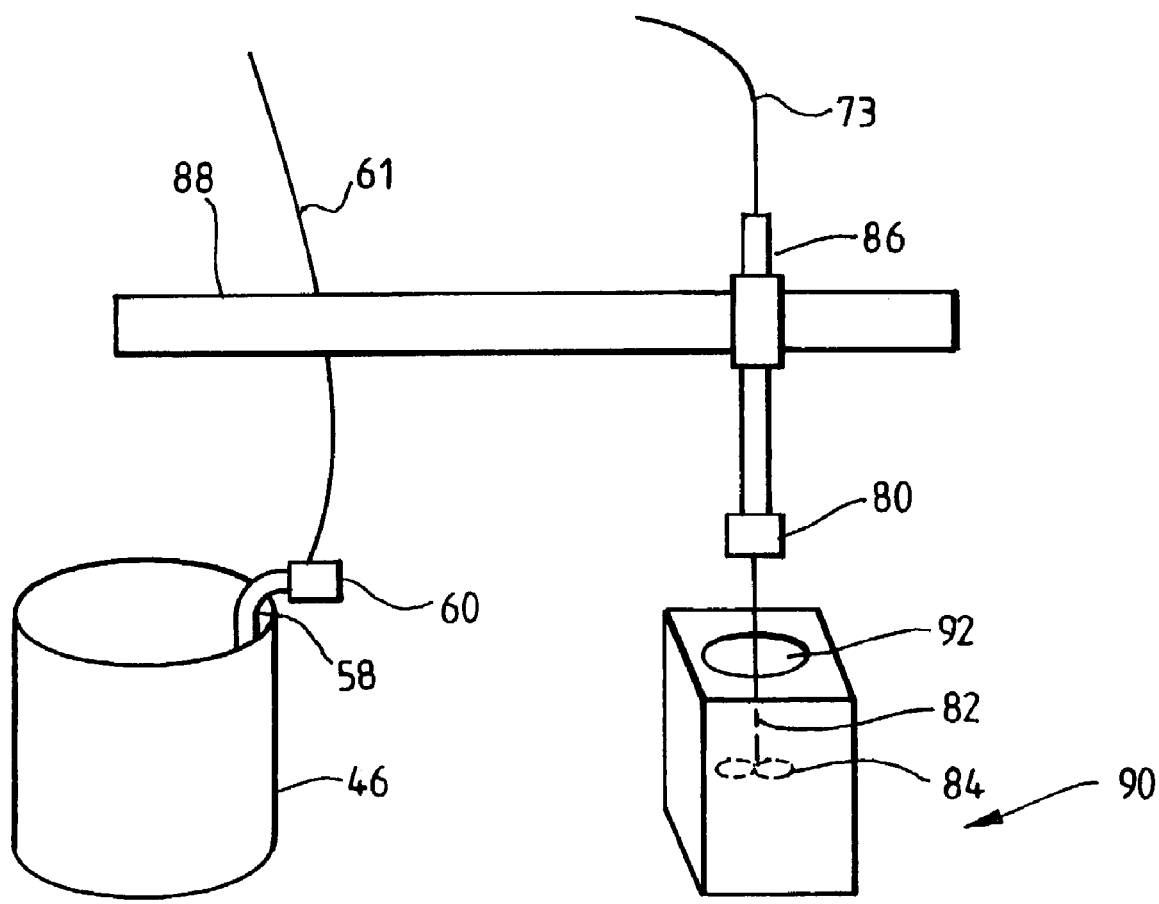
FIG. 4 is a side view of part of the fluid formulation system of the invention which shows the mixing vessel and the cleaning chamber. The mixing means is inserted into the cleaning chamber.

When a change is made from one type of fluid formulation to another, it is imperative to clean the mixer 56 so that successive fluid formulations are not contaminated by residue from the previous formulation. The computer 62 may be programmed to remove the mixer 56 from the mixing vessel 46 by activating the control means 86 to vertically retract mixer 56 from mixing vessel 46. Mixer 56 is then moved along support bracket 88 by any conventional mechanical, electoro-magnetic or hydraulic means to a position just over the top of cleaning chamber 90. When in this position, the control means 86 inserts mixer blades 84 and shaft 82 completely into the internal vessel 92, as shown in FIG. 4. Cleaning chamber 90 is then activated to perform a preprogrammed cleaning cycle. Once this cycle is complete, the mixer is retracted out of the cleaning chamber 90 and is then moved along support bracket 88 to a position directly over mixing vessel 46 to await instructions from computer 62 to enter the mixing vessel and begin its mixing function on a new formulation.

The invention claimed is:

1. A system for preparing a fluid formulation, wherein said fluid formulation is selected from the group consisting of emulsion, gel and colloidal fluids, comprising:
   a plurality of flexible conduits, each having an inlet end and an outlet end, said plurality of flexible conduits operatively disposed within at least one of a plurality of pump means,
   each inlet end of said plurality of flexible conduits disposed within one of a plurality of storage vessels, said storage vessels each containing a different liquid fluid formulation precursor ingredient,
   the outlet ends of said plurality of flexible conduits disposed to deliver each of the precursor ingredients into a mixing vessel,
   the at least one of the plurality of pump means situated between the storage vessels and the mixing vessel in order to transport an amount of each of the precursor ingredients from its respective storage vessel through its respective flexible conduit into the mixing vessel,
   a plurality of flow restrictors in operative communication with each of the plurality of flexible conduits to independently regulate the amount of each of the precursor ingredients being delivered to the mixing vessel,
   means for mixing the combined precursor ingredients into the fluid formulation within the mixing vessel,
   cleaning chamber, containing a cleaning fluid, located adjacent said means of mixing,
   support bracket for supporting said means for mixing within said mixing vessel, within said cleaning chamber, and between said mixing vessel and said cleaning chamber,
   linear actuator and control means capable of regulating vertical and lateral motion of said means for mixing along said support bracket,
   a computer in operative communication with said pump means, said plurality of flow restrictors, said linear actuator and control means and said mixing means,
   a sensor means disposed within the mixing means to quantitatively measure at least one of a plurality of physical properties of the fluid formulation during mixing, said physical properties selected from the group consisting of mass, volume, viscosity and pH, the sensor means converting the at least one of the plurality of the physical property measurements into at least one of a plurality of corresponding measured physical property values, and
   electronic sending means to transmit the at least one of the plurality of measured physical property values to the computer, wherein the computer receives the at least one of the plurality of the measured physical property values, compares each measured physical property value to a corresponding desired physical property value, said desired physical property value having been previously input into the computer database, and sends output signals to each one of the plurality of flow restrictors and the pump means to independently regulate the amount of precursor ingredient traversing through each respective flexible conduit into the mixing vessel.

2. The system of claim 1 wherein the pump means is a peristaltic pump.

3. An automated process for making a fluid formulation using the system of claim 1, wherein said fluid formulation is selected from the group consisting of emulsion, gel and colloidal fluids, comprising the steps of:
   inputting a fluid formulation recipe into the database of a computer, wherein said computer controls the automated process for making the fluid formulation, and wherein said recipe lists all of the precursor ingredients and process steps necessary to make the fluid formulation, wherein the recipe also comprises at least one of a plurality of desired physical property values of the fluid formulation,
   delivering a plurality of fluid formulation precursor ingredients to a mixing vessel in accordance with the directions provided by the computer, wherein each of said plurality of precursor ingredients traverses through one of a plurality of flexible conduits, said precursor ingredients being urged toward the mixing vessel via the action of a pump means, mixing the precursor ingredients in the mixing vessel by mixing means to generate a fluid formulation, stopping the automated process as directed by the computer when all of the precursor ingredients required by the recipe have been added to the mixing vessel and all of the mixing process steps included in the recipe have been performed, and removing the mixing means from the mixing vessel, conveying said mixing means to and inserting it into a cleaning vessel located in near proximity to the mixing vessel.

4. The automated process of claim 3 further comprising quantitatively measuring by sensor means located in the mixing vessel at least one of a plurality of physical properties of the fluid formulation during mixing, said physical properties selected from the group consisting of the mass, volume, viscosity and pH of the fluid formulation, and generating a corresponding measured physical property value for each of the plurality of measured physical properties, sending the at least one of the plurality of the measured physical property values to the computer, comparing each measured physical property value with its corresponding desired physical property value, said desired physical property value having been previously input into the computer database, sending output signals from the computer to each of a plurality of flow restrictors and the pump means to independently regulate the amount of each of the precursor ingredients being delivered to the mixing vessel, and shutting off the pump means and the mixing means when the combination of each of the plurality of measured physical property values corresponds to each of the plurality of the desired physical property values.

5. The process of claim 3 wherein the pump means is a peristaltic pump.

6. The process of claim 3 wherein the viscosity of the fluid formulation is from 1 centipoise to 10,000 poise.

* * * * *